(12) United States Patent
Hamann (10) Patent No.: US 11,325,919 B1
(45) Date of Patent: May 10, 2022

(54) SYNTHETIC NOVEL PYRROLOIMINOQUINONE ALKALOID AND METHOD OF USE

(71) Applicant: Mark T. Hamann, Mount Pleasant, SC (US)

(72) Inventor: Mark T. Hamann, Mount Pleasant, SC (US)

( * ) Notice: Subject to any disclaimer, the term of this patent is extended or adjusted under 35 U.S.C. 154(b) by 0 days.

(21) Appl. No.: 17/420,668

(22) PCT Filed: Jan. 9, 2020

(86) PCT No.: PCT/US2020/012841
§ 371 (c)(1),
(2) Date: Jul. 3, 2021

(87) PCT Pub. No.: WO2020/146569
PCT Pub. Date: Jul. 16, 2020

Related U.S. Application Data (60) Provisional application No. 62/790,143, filed on Jan. 9, 2019.

(51) Int. Cl.
*C07D 495/22* (2006.01)
*A61P 35/00* (2006.01)

(52) U.S. Cl.
CPC ............ *C07D 495/22* (2013.01); *A61P 35/00* (2018.01)

(58) Field of Classification Search
CPC .............................. C07D 495/22; A61P 35/00
See application file for complete search history.

(56) References Cited

U.S. PATENT DOCUMENTS

| | | |
|---|---|---|
| 2005/0187240 A1 | 8/2005 | Pettit et al. |
| 2010/0144779 A1 | 6/2010 | Velu et al. |

OTHER PUBLICATIONS

Zou, et al., Computationally Assisted Discovery and Assignment of a Highly Strained and PANC-1 Selective Alkaloid from Alaska's Deep Ocean, J. Am. Chem. Soc., 141, 4338-4344 (2019) (Year: 2019).*
PCT/US2020/012821 Written opinion of the international authority dated Mar. 30, 2020.

* cited by examiner

*Primary Examiner* — Erich A Leeser
(74) *Attorney, Agent, or Firm* — Veritay Group IP, PLLC; Susan B. Fentress; Liam O'Donnell (57) ABSTRACT

Aleutianamine represents the first in a new class of pyrroloiminoquinone alkaloids possessing a highly strained multi-bridged ring system, discovered from *Latrunculia (Latrunculia) austini* Samaai, Kelly & Gibbons, 2006 (class Demospongiae, order Poecilosclerida, family Latrunculidae) recovered during a NOAA deep-water exploration of the Aleutian Islands. Aleutianamine exhibited potent and selective cytotoxicity toward solid tumor cell lines including pancreatic cancer (PANC-1) with an IC50 of 25 nM and colon cancer (H116) with IC50 of 1 µM.

12 Claims, 5 Drawing Sheets

Aleutianamine-1

| Type | DP4+ | CMAE | CTAD |
|---|---|---|---|
| Proton | 98.96% | 0.17 | 1.86 |
| Carbon | 100.00% | 2.66 | 47.90 |
| Both | 100.00% | 2.83 | 49.76 |

Aleutianamine-1'

| Type | DP4+ | CMAE | CTAD |
|---|---|---|---|
| Proton | 1.04% | 0.19 | 2.12 |
| Carbon | 0.00% | 3.33 | 59.90 |
| Both | 0.00% | 3.52 | 62.02 |

Aleutianamine-1"

| Type | DP4+ | CMAE | CTAD |
|---|---|---|---|
| Proton | 0.00% | 0.33 | 3.64 |
| Carbon | 0.00% | 5.12 | 92.11 |
| Both | 0.00% | 5.45 | 95.75 |

SYNTHETIC NOVEL PYRROLOIMINOQUINONE ALKALOID AND METHOD OF USE

CROSS REFERENCE TO RELATED APPLICATIONS

This application is a § 371 National Stage Application of PCT/US20/12841 application filed Jan. 9, 2020 and U.S. provisional patent application Ser. No. 62/790,143 filed Jan. 9, 2019, under 35 U.S.C. § 111(a) (hereby specifically incorporated herein by reference).

STATEMENT REGARDING FEDERALLY SPONSORED RESEARCH OR DEVELOPMENT

None.

REFERENCE TO SEQUENCE LISTING, A TABLE FOR A COMPUTER PROGRAM LISTING, COMPACT DISC APPENDIX

None.

BACKGROUND OF THE INVENTION

Field of the Invention

This invention relates to a new class of semi-synthetically and synthetically derived alkaloids with potent and selective targeting cancer in vitro, specifically pancreatic, breast and glioblastoma cancer cells.

Description of the Related Art

Pancreatic cancer is one of the most deadly cancers with a 5-year survival rate of less than 8%.[1] The only curative therapy is surgery for which only 15-20% of patients are eligible and of those about 20% are long-term survivors.[2] For metastatic disease there are essentially only two chemotherapy options: the multidrug regime FOLFIRINOX and gemcitabine.[2] Although standard chemotherapeutic treatments for pancreatic cancer add months to a patient's overall survival time, there is little improvement in survival rates.[3] This disparity, compared to other cancer types, has led to the projection that pancreatic cancer will become the second most deadly cancer in the United States by 2030, surpassed only by lung cancer.[4] Any improvements in treatment strategies will come as a much-needed reprieve to patients diagnosed with this uniquely-challenging disease.

Natural products have provided a diversity of valuable drugs in addition to the identification of key targets for the control of cancer.[5-8] It has been estimated that up to 50% of all present day therapeutics are derived from natural products, and in the case of cancer, the number is near 75%.[9-10] The plant derived chemotherapy paclitaxel is one of the most highly documented treatments from a natural source and marine invertebrates have provided lead molecules such as discodermolide,[11] halichondrin B, didemnin B, and the dolastatins, all in various stages of development.[12-15] Among the unique marine derived ring systems, the pyrroloiminoquinone alkaloids have been studied for decades.[16-18] The promising biological activities for members of this class and their unique structures have made these molecules prime targets for syntheses[19-21] and biosynthesis studies.[22-25]

Our discovery of new discorhabdins[26] and related metabolites[27] from the North Pacific sponge *Latrunculia* (*Latrunculia*) *austini* Samaai, Kelly & Gibbons, 2006 (class Demospongiae, order Poecilosclerida, family Latrunculiidae), recently reviewed and redscribed in a review of family Latrunculiidae,[28] prompted a recollection during the NOAA deep ocean survey followed by a detailed assessment of the NCI repository of this genus group to facilitate the discovery of new brominated alkaloids. Identification of new molecules early in the workflow using MS, NMR and computational tools minimizes time, effort, and the cost of large screening campaigns.[29] A variety of dereplication strategies have been developed in recent years including HPLC-MS, -NMR, and -NMR-MS or bioactivity fingerprints, such as cytological profiling or BioMAP,[30-31] however, few are as efficient and useful as the recently developed network analysis tools for the visualization of observed molecules as familial groupings generated using MS fragmentation data assessed via vector correlations and displayed as an MS/MS network.[32] The visualization of networks using Cytoscape enables the direct observation of similarities as well as differences between two or more samples in which similar entities within the network are clustered together while disparate or unique entities are grouped separately.[33] Using this approach the discovery of aleutianamine and assessment of the NCI repository was strongly facilitated as aleutianamine is a minor constituent co-occurring with other highly biologically active molecules. Computational approaches, in conjunction with spectroscopic methods, provide a powerful and emerging method for the assignment of atom connectivity, relative configuration, and absolute configuration of complex molecules.[34-35] Highly noteworthy is the protocol developed recently by Martin and Williamson et al.[36] incorporating anisotropic NMR parameters with computational approaches to determine the structures of complex natural products. The successful characterization of karlotoxin 2 (KmTx2) followed by KmTx8 and KmTx9 was supported by NMR chemical shift calculation tools including GIAO and DP4+ probability studies in conjunction with HSQC studies.[37-40] Excited-state TDDFT calculations were applied here in conjunction with experimental ECD spectroscopy to determine the absolute configurations of the natural product.[41-45] We also used comparison of experimental and calculated $^1H$ and $^{13}C$ NMR chemical shifts of different regioisomers matching the chemical formula of aleutianamine to help verify that the structure was correctly assigned. The approach described here involves orchestration of a number of computational methods in combination with spectroscopic analyses leading to the discovery and establishment of the well-defined structure for aleutianamine.

BRIEF SUMMARY OF THE INVENTION

Synthetic Aleutianamine represents the first in a new class of pyrroloiminoquinone alkaloids possessing a highly strained multi-bridged ring system. Aleutianamine exhibits potent and selective cytotoxicity toward solid tumor cell lines. such as for example: pancreatic cancer (PANC-1) with an IC50 of 25 nM and colon cancer (H116) with IC50 of 1μ. Aleutianamine is depicted by the formula R₁ = S, O, CH₂, Se
R₂ = F, Cl, Br, I, H (formula I) or a pharmaceutically acceptable salt thereof and a pharmaceutically acceptable carrier or a pharmaceutically acceptable excipient, wherein R.sub.1=S, O, CH2, and Se and R.sub.2=F, Cl, Br, I and H. The present invention provides pyrroloiminoquinone alkaloids possessing a highly strained multi-bridged ring system, as pharmaceutical formulations and compositions: for example, a structural analog is shown in formula (II)

formula (II) or a pharmaceutically acceptable salt thereof. In another embodiment, this invention also relates to a method for synthesizing a pyrroloiminoquinone alkaloids possessing a highly strained multi-bridged ring system.

DETAILED DESCRIPTION OF THE INVENTION

Aleutianamine represents the first in a new class of pyrroloiminoquinone alkaloids possessing a highly strained multi-bridged ring system, discovered from *Latrunculia* (*Latrunculia*) *austini* Samaai, Kelly & Gibbons, 2006 (class Demospongiae, order Poecilosclerida, family Latrunculiidae) recovered during a NOAA deep-water exploration of the Aleutian Islands. Only trace quantities in a few samples from the Genus *Latrunculia* were identified. Our explanation is that the material is a degradation product discorhabdin A that may only occur in anoxic regions of the ocean with the help of the high pressure and cold conditions. As only trace quantities exist in nature and only under certain specialized environments any pharmaceutical product would need to be synthesized. The term synthetic includes both synthetically and semi-synthetically derived Aleutianamine. Semi-synthetically means starting with a complex natural product that is as close to the desired product as possible to reduce the number of overall steps.

The molecule was identified with the guidance of MS, NMR, and Molecular Ion Networking (MoIN) analysis. The structure of Aleutianamine was determined using extensive spectroscopic analysis in conjunction with computationally assisted quantitative structure elucidation tools The present invention provides pyrroloiminoquinone alkaloids possessing a highly strained multi-bridged ring system as pharmaceutical formulations and composition shown in formula (I) and methods for the use of pyrroloiminoquinone alkaloids possessing a highly strained multi-bridged ring system.

Additionally, methods are provided for the use of pyrroloiminoquinone alkaloids possessing a highly strained multi-bridged ring system as therapeutic agents to inhibit cancer cells. Aleutianamine exhibited potent and selective cytotoxicity toward solid tumor cell lines including pancreatic cancer (PANC-1) with an $IC^{50}$ of 25 nM and colon cancer (H116) with $IC^{50}$ of 1 µM.

These pyrroloiminoquinone alkaloids possessing a highly strained multi-bridged ring system can be used to treat medical conditions by administering to a subject suffering from or susceptible to such a disease or condition, a therapeutically effective amount of the compound, a derivative or analog, or an optical isomer or racemate or tautomer thereof or a pharmaceutically acceptable salt thereof or optimally in a mixture with a pharmaceutically acceptable diluent or carrier. For example, the novel subject matter includes a method of inhibiting colon, liver, brain, prostate, breast, lung, ovary, rectum and pancreatic cancer cells by contacting the cells with an inhibitory amount of a compound of the formula: I or II.

The pharmaceutical formulation or compositions can be administered via any suitable therapeutic method and technique presently or prospectively known to those skilled in the art. Further, the compounds for use in this invention have use as starting materials for the preparation of other useful drug products and compositions.

The dosage administered to a host will be dependent upon the disorder, the type of host involved, its age, weight, health, kind of concurrent treatment, if any, frequency of treatment and therapeutic ratio.

The compounds of the subject invention can be formulated according to known methods for preparing pharmaceutically useful compositions. Formulations are described in detail in a number of sources that are well known and readily available to those skilled in the art. For example, Remington's Pharmaceutical Science by E. W. Martin describes formulations that can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as the active ingredient, an effective amount of one or more of the subject compounds and one or more non-toxic, pharmaceutically acceptable carriers or diluents, can be used by persons of ordinary skill in the art. The compositions may be administered to the subject at one time or over a series of treatments.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from serum levels and bio-chemical assays. For example, a dose can be formulated in animal models to achieve a circulating concentration range that includes the EC50 (the dose where 50% of the subjects show the desired effects) as determined in assays. Such information can be used to more accurately determine useful doses in humans and animals.

A therapeutically effective dose refers to that amount of the compound resulting in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds that exhibit high therapeutic indices are preferred. The data obtained from the receptor binding assays and animal studies can be used in formulating a range of dosage for use in animal and human subjects. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's or subject's condition. (See e.g. Fingl et al., 1975, in "The Pharmacological Basis of Therapeutics", Ch. 1 p 1). Dosage amount and interval may be adjusted individually to provide plasma levels of the active moiety that are sufficient to maintain the desired effects.

In cases of local administration or selective uptake, the effective local concentration of the drug may not be related to plasma concentration. The amount of composition administered will, of course, be dependent on the subject being treated, on the subject's weight, the severity of the affliction, the manner of administration and the judgment of the prescribing physician. In a preferred embodiment, efficacy ranges from about 0.1 mg/kg to 100 mg/kg daily. The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes. Pharmaceutical compositions for use in accordance with the present invention thus may be formulated in a conventional manner using one or more physiologically acceptable carriers comprising excipients and auxiliaries that facilitate processing of the active compounds into preparations that can be used pharmaceutically. Proper formulation is dependent upon the route of administration chosen. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art. For oral administration, the compounds can be formulated readily by combining the active compounds with pharmaceutically acceptable carriers well known in the art. Such carriers enable the compounds of the invention to be formulated as tablets, pills, pellets, dragees, capsules, liquids, gels, syrups, slurries, suspensions and the like, for oral ingestion by a patient to be treated. Pharmaceutical preparations for oral use can be made as solid excipient, by optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxy-methylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in a conventional manner. For administration by inhalation, the compounds for use according to the present invention are conveniently delivered in the form of an aerosol spray presentation from pressurized packs or a nebulizer, with the use of a suitable propellant, e.g., dichlorodifluoromethane, trichloro-fluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use. More specially, this molecule is a very good candidate for applications using conventional IV delivery, delivery as an antibody drug conjugate and hyperthermic intraperitoneal chemotherapy (HIPEC). The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials as an emulsion in an acceptable oil or ion exchange resins, or as sparingly soluble derivatives, for example, as a sparingly soluble salt. A pharmaceutical carrier for the hydrophobic compounds of the invention is a cosolvent system comprising benzyl alcohol, a nonpolar surfactant, a water-miscible organic polymer, and an aqueous phase. Naturally, the proportions of a co-solvent system may be varied considerably without destroying its solubility and toxicity characteristics. Furthermore, the identity of the co-solvent components may be varied. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed. The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The terms: compound, formulation or the specific compounds listed by name can be interpreted to include salts with pharmaceutically compatible counterions. The phrase "pharmaceutically acceptable salts" refers to the relatively non-toxic inorganic and organic acid addition salts, and base addition salts, of the compounds of the present invention. These salts may be prepared in situ during final isolation and purification of the compounds. In particular, the acid addition salts may be prepared by separately reacting the purified compound in its clean form with an organic or inorganic acid and isolating the resultant salt. Examples of acid addition salts include hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptanate, lactobionate, sulfamates, malonates, salicylates, propionates, methylenebis-beta-hydroxynaphthoates, gentisic acid, isethionates, di-p-toluoyltartrates, methanesulfonates, ethanesulfonates, benzenesulfonates, p-toluenesulfonates, cyclohexyl sulfamates and quinate lauryl sulfonate, and the like. (See for example S. M. Berge et al. "Pharmaceutical Salts" J. Pharm. Sci, 66: p. 1-19 (1977) which is incorporated herein by reference). The acid addition salts may also be prepared by separately reacting the purified compound in its acid form with an organic or inorganic base and isolating the resultant salt. Acid addition salts include amine and metal salts. Suitable metal salts comprise the salts of sodium, potassium, calcium, barium, zinc, magnesium and aluminium. Sodium and potassium salts are preferred. Suitable inorganic base addition salts are prepared from metallic bases which comprise sodium hydride, sodium hydroxide, potassium hydroxide, calcium hydroxide, aluminium hydroxide, lithium hydroxide, magnesium hydroxide, zinc hydroxide. Suitable amine base addition salts are prepared from amines which have sufficient alkalinity to form a stable salt, and preferably comprise the amines which are frequently used in medicinal chemistry due to their low toxicity and their acceptability for medical use: ammonia, ethylenediamine, N-methylglucamine, lysine, arginine, ornithine, choline. N,N'-dibenzylethylenediamine, chloroprocaine, diethanolamine, procaine, N-benzylphenethylamine, diethylamine, piperazine, tris(hydroxymethyl)-aminomethane, tetramethylammonium, hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, for example lysine and arginine, and dicyclohexylamine, and the like. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms. Suitable routes of administration may, for example, include oral, rectal, transmucosal, transdermal, or intestinal administration; parenteral delivery, including intramuscular, subcutaneous, intramedullary injections, as well as intrathecal, direct intraventricular, intravenous, intraperitoneal, intranasal, or intraocular injections. A suitable carrier can include sterile water. Alternately, one may administer the compound in a local rather than systemic manner, for example, via injection of the compound directly into an affected area, often in a depot or sustained release formulation. Furthermore, one may administer the drug in a targeted drug delivery system, for example, in a liposome coated with an antibody specific for affected cells. The liposomes will be targeted to and taken up selectively by the cells. The drugs may also be administered in a prodrug form in which a hydrolysable, oxidizable or reducible moiety has been formed at one or more reactive sites in the molecule. These include but are not limited to esters, sulphates, phosphates or any other group which can be readily metabolized to generate the active form of the drug. In veterinarian application the pharmaceutical composition can be delivered as a pellet or powder. The inactive ingredient can be, for example, alfalfa, apple flavor, cane molasses, propionic acid, sorbitol, Vitamin E complex and wheat germ meal.

The novel subject matter also includes a method for synthesizing a new class of pyrroloiminoquinone alkaloids possessing a highly strained multi-bridged. The method including the steps of converting a Discorhabdin A to Aleutianamine through a concerted rearrangement catalyzed through activation of the sulfur, removal of the vicinal proton, 1,4 addition and elimination of quinone, hydride transfer to generate a new double bond and elimination of the OH group vicinal to the amine of the iminoquinone.

The assignment of structure for Aleutianamine was accomplished using NMR, MS, ECD and computational approaches. Structure verification was completed using DFT calculations followed by the DP4+ calculations.

The frozen sponges were extracted with ethanol and the extract was analyzed by LCMS. NCI samples MoIN analyzing. Each compound from six standards and the 10 crude ethanol extracts of *Latrunculia* sp. from NCI were solubilized in 100% MeOH to 1 mg/ml. The injected samples were chromatographically separated using an Agilent analytical UHPLC (Santa Clara, Calif.) using a 100×4.6 mm Kinetex 1.7 µM, C8, chromatography column (Phenomenex Torrance, Calif.), 1 mL/min flow rate, mobile phase A 99.9% water (VWR, LC-MS grade), 0.1% formic acid (VWR); mobile phase B 99.9% acetonitrile (VWR, LC-MS grade), 0.1% formic acid (VWR); with the following gradient: 0-1 min 5% B, 1-15 min 100% B, 15-25 min, 100% B, 26-30 min, 5% B for all samples.

The assignment of structure for Aleutianamine was accomplished using NMR, MS, ECD and computational approaches. Extensive 2 dimensional NMR studies including J based analysis was used to assign the structure of the molecule. Structure verification was completed using DFT calculations followed by the DP4+ calculations a chemical shift analysis tool.

Table. *Latrunculia* species in the Natural Products Branch of the National Institutes of Health/National Cancer Institute repository, from which extracts were assayed for the presence of aleutianamine.

| Taxon name | Locality |
| --- | --- |
| *Latrunculia* (*Biannulata*) *procumbens* Alvarez etal., 2002 | Northland, Northeastern New Zealand |
| *Latrunculia* (*Biannulata*) *procumbens* Alvarez etal., 2002 | Northland, Northeastern New Zealand |
| *Latrunculia* (*Latrunculia*)? *triverticillata* Alvarez etal., 2002 | Chatham Island, Southeastern New Zealand |
| *Latrunculia* (*Biannulata*) *purpurea* Carter, 1881 | Albany, Western Australia |
| *Latrunculia* (*Biannulata*) *purpurea* Carter, 1881 | Victoria, Southeastern Australia |
| *Latrunculia* (*Biannulata*) *kaakaariki* Alvarez etal., 2002 | Northland, Northeastern New Zealand |
| *Latrunculia* (*Latrunculia*) *biformis* Kirkpatrick, 1908 | McMurdo Sound, Antarctica |
| *Latrunculia* (*Latrunculia*) sp. nov. | Tasmania, Southern Australia |
| *Latrunculia* (*Latrunculia*) *fiordensis* Alvarez etal., 2002 | Fiordland, Southwest New Zealand |
| *Latrunculia* (*Biannulata*) *lunaviridis* Samaai etal., 2003 | Western Cape, South Africa |
| *Latrunculia* (*Latrunculia*) *hamanni* Kelly et al., 2016 | Aleutian Islands, Alaska |

Figure 1A:
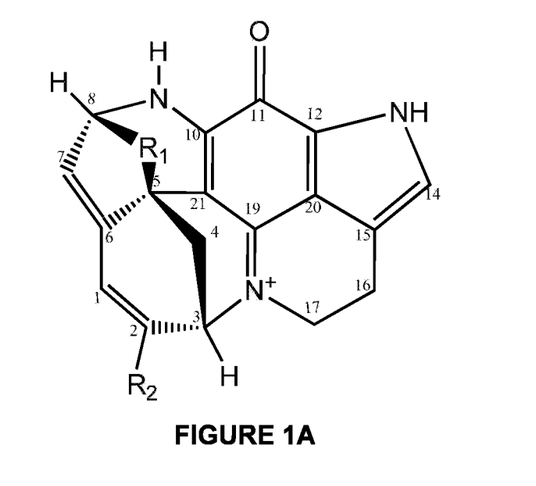
FIGS. 1A and 1B. shows the enantiomeric pair of the aleutianamine molecule. Partial bio-isosteric replacements have been completed at the sulfur and bromine atoms. In addition, reduction of any or all double bonds and the bio-isosteric replacement of each hydrogen on the ring systems with OH, SH, N, F, Cl, Br, I, D, small alkyl groups is contemplated as being within the scope of the inventive subject matter.
Figure 1B:
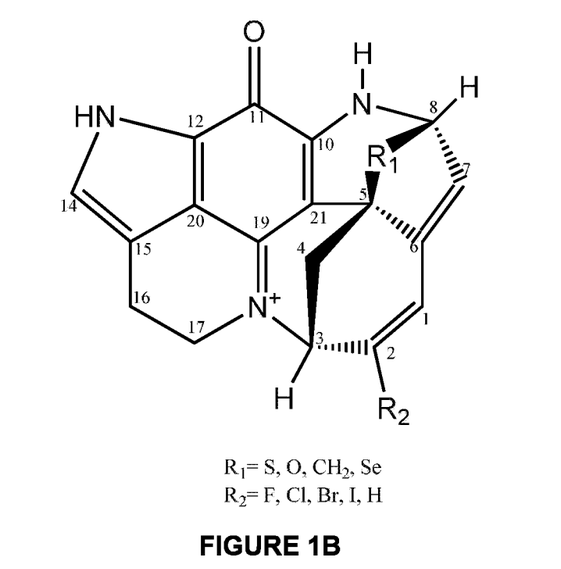
Figure 2:
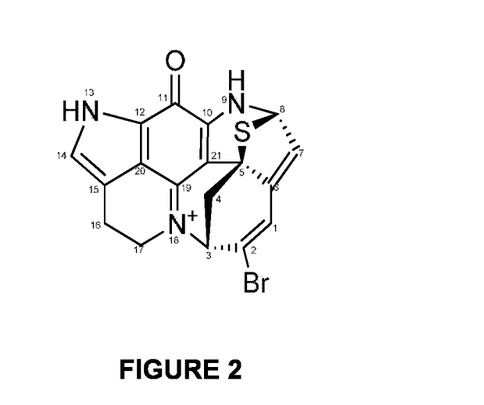
FIG. 2. shows the configuration of aleutianamine.
Figure 3:
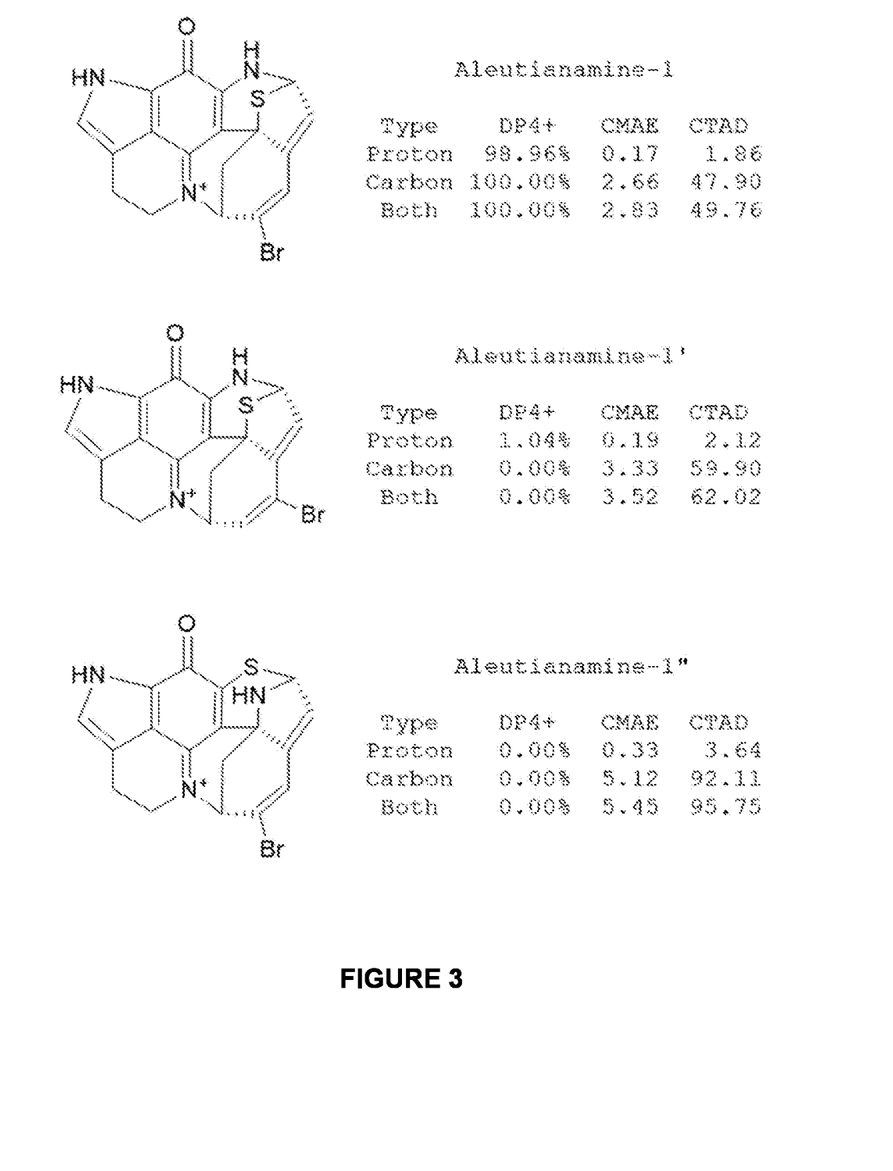
FIG. 3. shows the completed DP4+ calculations which were used to verify the NMR assigned structure. DFT calculation followed by the DP4+ calculations are becoming a routine approach to the assignment and verification of NMR assigned structure. These results show that the calculated NMR values are in perfect agreement with our assigned structure for aleutianamine.

Now referring to FIG. 3, the calculated chemical shifts of aleutianamine-1, aleutianamine-1', and aleutianamine-1" were compared to the experimental $^1$H and $^{13}$C NMR chemical shifts via the corrected mean absolute error (CMAE), the corrected total absolute deviation (CTAD), as well as DP4+ probability chemical shift analysis s2 The CMAE and CTAD results showed that aleutianamine-1 was the most probable isomer. These results were corroborated by the DP4+ statistical analysis, which predicted aleutianamine-1 to be the correct regioisomer with a probability of 100%, based on utilization of both $^1$H and $^{13}$C NMR data. Collectively, the excellent agreement between NMR spectroscopic and computational data strongly supported the (3R,5R,8S) absolute configuration of aleutianamine and its 2-bromo substituent.

| Boltzmann populations and relative binding free energies of conformations of aleutianamine-1. | | |
| --- | --- | --- |
| Species | Boltzmann Population (%) | ΔG* (kJ/mol) |
| Aleutianamine-1 (1) | 86.7 | 0 |
| Aleutianamine-1 (2) | 13.3 | 4.65 |

| Boltzmann populations and relative binding free energies of conformations of aleutianamine-1'. | | |
| --- | --- | --- |
| Species | Boltzmann Population (%) | ΔG* (kJ/mol) |
| Aleutianamine-1' (1) | 89.58 | 0 |
| Aleutianamine-1' (2) | 10.42 | 5.33 |

| Boltzmann populations and relative binding free energies of conformations of aleutianamine-1". | | |
| --- | --- | --- |
| Species | Boltzmann Population (%) | ΔG* (kJ/mol) |
| Aleutianamine-1" (1) | 84.03 | 0 |
| Aleutianamine-1" (2) | 15.97 | 4.12 |

Example: Semi-synthetic Pathway of Aleutianamine

Figure 4:
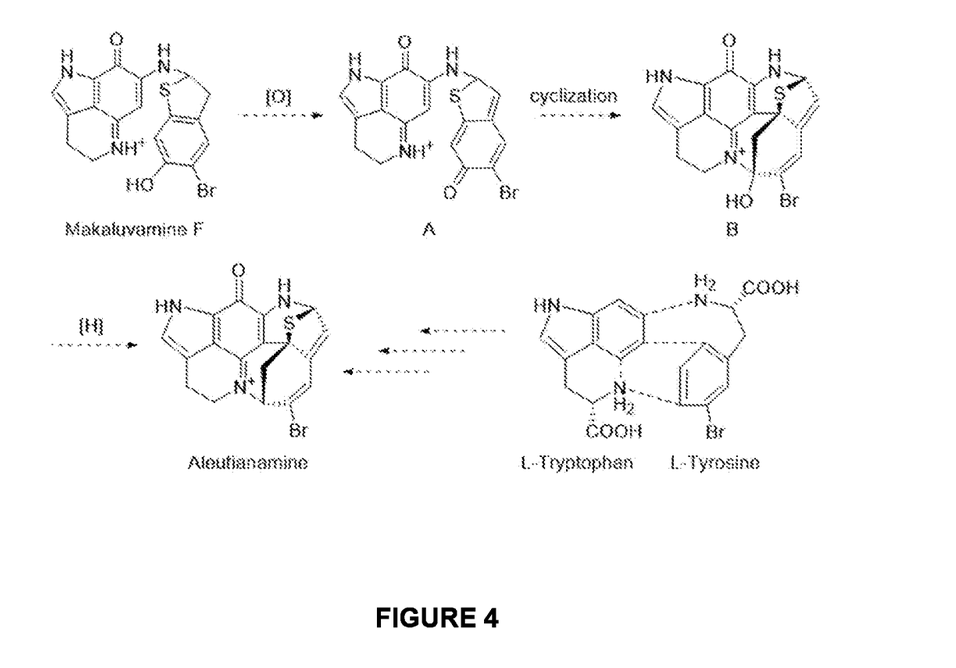
FIG. 4. shows the di-peptidic construction of the molecule without rearrangement of carbon.

Now referring to FIG. 4, the complex molecular architecture of aleutianamine appears to have arisen from only two standard amino acids L-tryptophan and L-tyrosine generating orthogonal ring systems without the rearrangement of carbon. FIG. 4 shows structural homology and a general biosynthetic route to the formation of Aleutianamine from two common amino acids, L tryptophan and L tyrosine with the addition of a sulfur atom from cysteine. These two key amino acids are critical to the formation of a number of iminoquinone alkaloids found in sponges. The general biosynthetic processes in this formation involves, oxidation, reduction, hydration and dehydration reactions without the rearrangement of carbon atoms. This process provides a general biomimetic approach that can be utilized to transform a variety of natural starting materials into Aleutianamine. Starting materials include but are not limited to: tryptophan, tyrosine, a Discorhabdin, Makaluvic acid, Makaluvone, Makaluvamines, Batzellines, lsobatzellines, Secobatzellines, Damirones, Tsitsikammamines, Veiutamine, Wakayin, Zyzzyanones alkaloids as well as other iminoquinone and pyrroloiminoquinone alkaloids. (Please see Chemical Reviews "Discorhabdins and Pyrroloiminoquinone-related alkaloids" by Hu et al. 2011, pp 5465-5488.

More specifically, the phenolic moiety of makaluvamine F serves as a precursor and undergoes oxidation to form quinone methide A. A Stork-type enamine Michael addition/cyclization followed by an imine cyclization would lead to B with the novel azabicyclo [3.3.1] nonane ring system constructed. Reduction of the 1-aminoethan-1-ol functionality would furnish the structure of aleutianamine.

Another semi-synthetic precursor is discorhabdin A, found in abundance in this species.

(1)

Discarhabdin A

Figure 5:
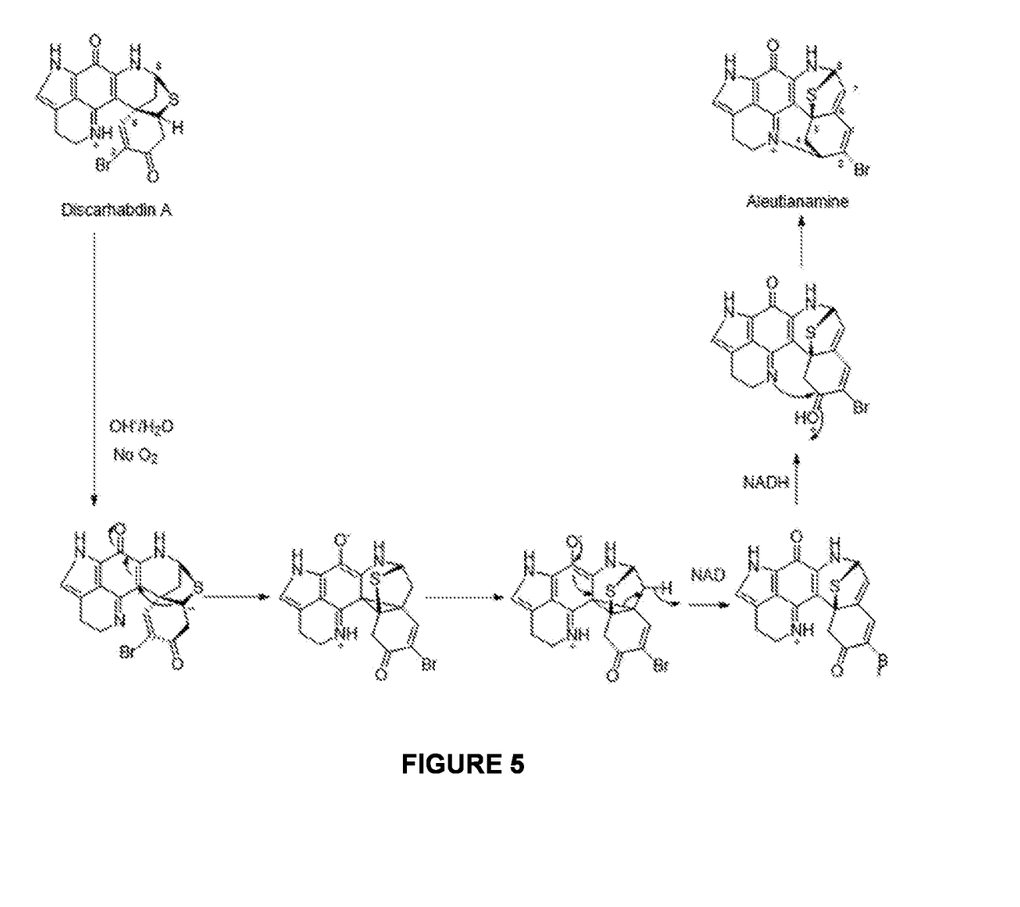
FIG. 5. shows the mechanistic transformation of Aleutianamine to Discorhabdin A under the unique conditions of high pressure, cold temperatures and anoxic conditions found in certain marine environments

An example of the biosynthetic conversion from discorhabdin A to aleutianamine is shown in FIG. 5. A process for the synthesis of Aleutianamine (II) involves the activation of sulfur through metal chelation or oxidation will stabilize a vicinal anion.

(3)

Reformation of the amino quinone will break the cyclopropyl intermediate to form an olefin in conjugation with alpha-beta unsaturated carbonyl.

(4)

(5)

This process results in a loss of a hydride which can be captured with NAD to form NADH. This rearrangement then moves the carbonyl carbon of the tyrosine closer to the nitrogen of the amino quinone leading to the formation of a Schiff's base related intermediate (6)

(2)

The stabilized anion can then undergo conjugate 1,4 addition with the amino quinone to form a cyclopropyl intermediate.

followed by dehydration and the formation of aleutianamine. This process is carried out under an inert atmosphere with NAD or a hydride transfer catalyst. Pressure can be utilized to encourage the addition reaction to formula (1) wherein R1 and R2 are independently sulfur, oxygen, nitrogen, carbon or selenium. R2 can also be fluorine, chlorine, bromine, or iodine. One or more olefins in the molecule maybe reduced and any hydrogen throughout the molecule can be independently replaced with deuterium, oxygen, sulfur, fluorine, chlorine, bromine, iodine or short chain alkyl. The counter ion in the molecule can be any common anion used to facilitate the delivery of the molecule.

Example: Bioassay

Aleutianamine, with its unique ring system, showed solid tumor selectivity in a differential cytotoxicity zone assay used for discovery of solid tumor selective anticancer leads.[25] Selectivity of cell killing was noted for murine colon cancer 38, human breast cancer MCF-7, human prostate cancer LNCaP, and human pancreatic cancer PANC-1 compared to both murine and human leukemia cells which are typically more sensitive. This breadth of selectivity is unusual for active compounds which usually demonstrate selectivity to only one of the cell types assayed. The IC5a value for aleutianamine formula II tested against human HCT-116 colon cancer cells was 1 μM and against PANC-1 pancreatic cancer cells were 25 nM, indicating significant potency and selectivity.

Clonogenic studies were carried out using HCT-116 cells to define the concentration-survival relationship as a function of exposure time.[26] The endpoint used, $_tS_{10}$ (10% survival of clonogenic cells for exposure time t) provides information essential for future preclinical therapeutic studies. These clonogenic studies based on formula II yielded a $_2S_{10}$ value of >5 μM; a $_{24}S10$ value of 0.75 μM; and a $_{168}S_{10}$ value of 0.1 μM. The clonogenic data indicated that, depending upon the pharmacokinetics and maximum tolerated dose of aleutianamine, a chronic treatment might be expected to be efficacious. The principal structural feature of discorhabdin is the core of a planar iminoquinone moiety which has been shown to intercalate and cleave DNA as well as inhibit the action of topoisomerase II.[16] The makaluvamines have been shown to be topoisomerase II inhibitors acting via cleavable complex formation, or via the direct induction of DNA double-strand breaks. Makaluvamines A and C are reported to decrease tumor size in a solid human tumor model.[53] However, discorhabdins A and C exhibited no inhibition of topoisomerase II despite their significant cytotoxicity with the same core iminoquinone skeleton supporting a dual mechanism against cancer.[16] Based on the data generated aleutianamine showed significantly higher cytotoxicity than discorhabdin A towards cancer cell lines and demonstrated selective inhibition to pancreatic cancer cell lines. Compounds shown in Formula I are simple modifications and bio-isosteres and would have similar activity to the compound of formula II.

TABLE 1

| Compound | Conc. | L1210 | Colon 38 | CFU-GM | H-116 | H-125 | MCF-7 | LNCaP | OVC-5 | U251N | MDA | PANC-1 | CEM |
|---|---|---|---|---|---|---|---|---|---|---|---|---|---|
| DMSO | | 0 | 0 | | 0 | 0 | 0 | 0 | 0 | 0 | 0 | 0 | |
| Ecdysone | 2 mg/ml | 0 | 0 | | 0 | 0 | 0 | 0 | 0 | 0 | 0 | 0 | |
| Aleutian Island akaloid | 2 mg/ml | 950 | >1000 | | >1000 | | | | | | | | |
| Aleutian Island akaloid | ¼ | 700 | >1000 | >1000 | 950 | >1000 | >1000 | | 900 | >1000 | >1000 | | 900 |
| Aleutian Island akaloid | 1/16 | 500 | 900 | >1000 | 600 | 900 | >1000 | 1000 | 700 | 850 | 800 | >1000 | 750 |
| Aleutian Island akaloid | 1/64 | 250 | 450 | 750 | 250 | 400 | 600 | 500 | 350 | 700 | 500 | 650 | 350 |
| Karlotoxin 2 | 2 mg/ml | 150 | 200 | | 200 | 100 | 200 | 400 | 200 | 150 | 200 | 200 | 100 |
| Discorhabdin A | 2 mg/ml | 1000 | 750 | | >1000 | | | | | | | | |
| Discorhabdin A | ¼ | 300 | 800 | >1000 | 900 | 950 | 800 | | 700 | 300 | 1000 | 450 | 450 |
| Discorhabdin A | 1/16 | 250 | 700 | 300 | 500 | 750 | 600 | 500 | 500 | 300 | 500 | 150 | 100 |
| Discorhabdin A | 1/64 | | | | | 400 | 350 | 250 | 200 | 200 | 300 | 100 | 50 |

Figure.
Aleutian Alkaloid X and zones of inhibition (mm) against various cancer cell types revealing PANC-1 selectivity (detailed in Aim 3a).
DMSO and ecdysone are included as negative controls and discorhabdin and karlotoxin as positive controls.

Table 1 shows the significant and selective zones of inhibition for PANC-1 (pancreatic cancer), U251 N (glioblastoma) and MCF-7 (drug resistant breast cancer). Aleutianamine (Aleutian Island Alkaloid) is highly potent and selective for pancreatic and breast cancer as well as gliobastoma. DMSO and Ecdysone are negative controls, karlotoxin and Discorhabdin A are two potent and non-selective controls which are comparable to taxol. Discorhabdin A is the precursor to aleutianamine.

REFERENCES

1. Jemal, A.; Siegel, R.; Xu, J.; Ward, E. Cancer Statistics, 2010. *CA Cancer J. Clin.* 2010, 60, 277.
2. Castellanos, J. A.; Merchant, N. B. Intensity of follow-up after pancreatic cancer resection. *Ann. Surg. Oncol.* 2014, 21, 747.
3. Garrido-Laguna, I.; Hidalgo, M. Pancreatic cancer: from state-of-the-art treatments to promising novel therapies. *Nat. Rev. Clin. Oncol.* 2015, 12, 319.
4. Rahib, L.; Smith, B. D.; Aizenberg, R.; Rosenzweig, A. B.; Fleshman, J. M.; Matrisian, L. M. Projecting cancer incidence and deaths to 2030: the unexpected burden of thyroid, liver, and pancreas cancers in the United States. *Cancer Res.* 2014, 74, 2913. Erratum in *Cancer Res.* 2014, 74, 4006.
5. Kinghorn, A. D. Review of anticancer agents from natural products ACS Publications. 2015, 78, 2315.

6. Rayan, A.; Raiyn, J.; Falah, M. Nature is the best source of anticancer drugs: Indexing natural products for their anticancer bioactivity. *PloS one.* 2017, 12, 1.
7. Beck, A.; Goetsch, L.; Dumontet, C.; Corvaia, N. Strategies and challenges for the next generation of antibody-drug conjugates. *Nat. Rev. Drug. Discov.* 2017, 16, 315.
8. Xiao, H.; Verdier-Pinard, P.; Fernandez-Fuentes, N.; Burd, B.; Angeletti, R.; Fiser, A.; Horwitz, S. B.; Orr, G. A. Insights into the mechanism of microtubule stabilization by Taxol. *Proc. Natl. Acad. Sci. U.S.A.* 2006, 103, 10166.
9. Newman, D. J.; Cragg, G. M. Natural products as sources of new drugs over the 30 years from 1981 to 2010. *J. Nat. Prod.* 2012, 75, 311.
10. Newman, D. J.; Cragg, G. M. Natural products as sources of new drugs from 1981 to 2014. *J. Nat. Prod.* 2016, 79, 629.
11. Prota, A. E.; Bargsten, K.; Redondo-Horcajo, M.; Smith III, A. B.; Yang, C. P. H.; McDaid, H. M.; Paterson, I.; Horwitz, S. B.; Fernando Díaz, J.; Steinmetz, M. O. Structural basis of microtubule stabilization by discodermolide. *ChemBioChem* 2017, 18, 905.
12. Chakraborty, T. K.; Das, S. Chemistry of potent anticancer compounds, amphidinolides. *Current Medicinal Chemistry-Anti-Cancer Agents.* 2001, 1, 131.
13. Mayer, A. M.; Gustafson, K. R. Marine pharmacology in 2003-2004: anti-tumour and cytotoxic compounds. *Eur. J. Cancer.* 2006, 42, 2241.
14. Alonso, D.; Khalil, Z.; Satkunanthan, N.; Livett, B. Drugs from the sea: conotoxins as drug leads for neuropathic pain and other neurological conditions. *Mini. Rev. Med. Chem.* 2003, 3, 785.
15. Grimes, D. J. Oceans and human health: risks and remedies from the sea. *National Institute of Environmental Health Sciences:* 2009.
16. Hu, J.-F.; Fan, H.; Xiong, J.; Wu, S.-B. Discorhabdins and pyrroloiminoquinone-related alkaloids. *Chem. Rev.* 2011, 111, 5465.
17. Antunes, E. M.; Copp, B. R.; Davies-Coleman, M. T.; Samaai, T. Pyrroloiminoquinone and related metabolites from marine sponges. *Nat. Prod. Rep.* 2005, 22, 62.
18. Lin, S.; McCauley, E. P.; Lorig-Roach, N.; Tenney, K.; Naphen, C. N.; Yang, A.-M.; Johnson, T. A.; Hernadez, T.; Rattan, R.; Valeriote, F. A. Another Look at Pyrroloiminoquinone Alkaloids-Perspectives on Their Therapeutic Potential from Known Structures and Semisynthetic Analogues. *Mar. Drugs.* 2017, 15, 98.
19. Tohma, H.; Harayama, Y.; Hashizume, M.; Iwata, M.; Kiyono, Y.; Egi, M.; Kita, Y. The first total synthesis of discorhabdin A. *J. Am. Chem. Soc.* 2003, 125, 11235.
20. Aubart, K. M.; Heathcock, C. H. A biomimetic approach to the discorhabdin alkaloids: total syntheses of discorhabdins C and E and dethiadiscorhabdin D. *J. Org. Chem.* 1999, 64, 16.
21. Roberts, D.; Joule, J. A.; Bros, M. A.; Alvarez, M. Synthesis of Pyrrolo [4, 3, 2-de]quinolines from 6, 7-Dimethoxy-4-methylquinoline. Formal Total Syntheses of Damirones A and B, Batzelline C, Isobatzelline C, Discorhabdin C, and Makaluvamines A-D. *J. Org. Chem.* 1997, 62, 568.
22. Lill, R. E.; Major, D. A.; Blunt, J. W.; Munro, M. H.; Battershill, C. N.; McLean, M. G.; Baxter, R. L. Studies on the biosynthesis of discorhabdin B in the New Zealand sponge *Latrunculia* sp. B. *J. Nat. Prod.* 1995, 58, 306.
23. Miyanaga, A.; Janso, J. E.; McDonald, L.; He, M.; Liu, H.; Barbieri, L.; Eustaquio, A. S.; Fielding, E. N.; Carter, G. T.; Jensen, P. R. Discovery and assembly-line biosynthesis of the lymphostin pyrroloquinoline alkaloid family of mTOR inhibitors in Salinispora bacteria. *J. Am. Chem. Soc.* 2011, 133, 13311.
24. Amos, G. C.; Awakawa, T.; Tuttle, R. N.; Letzel, A.-C.; Kim, M. C.; Kudo, Y.; Fenical, W.; Moore, B. S.; Jensen, P. R. Comparative transcriptomics as a guide to natural product discovery and biosynthetic gene cluster functionality. *Proc. Natl. Acad. Sci. U.S.A* 2017, 114, 11121.
25. Jordan, P. A.; Moore, B. S. Biosynthetic pathway connects cryptic ribosomally synthesized posttranslationally modified peptide genes with pyrroloquinoline alkaloids. *Cell. Chem. Biol.* 2016, 23, 1504.
26. Na, M.; Ding, Y.; Wang, B.; Tekwani, B. L.; Schinazi, R. F.; Franzblau, S.; Kelly, M.; Stone, R.; Li, X.-C.; Ferreira, D. Anti-infective discorhabdins from a deep-water Alaskan sponge of the genus *Latrunculia*. *J. Nat. Prod.* 2009, 73, 383.
27. Zou, Y.; Hamann, M. T. Atkamine: A new pyrroloiminoquinone scaffold from the cold water Aleutian Islands *Latrunculia* sponge. *Org. Lett.* 2013, 15, 1516.
28. Kelly, M.; Sim-Smith, C.; Stone, R.; Samaai, T.; Reiswig, H.; Austin, W. New taxa and arrangements within the family Latrunculiidae (Demospongiae, Poecilosclerida). *Zootaxa,* 2016, 4121, 1.
29. Gerwick, W. H.; Moore, B. S. Lessons from the past and charting the future of marine natural products drug discovery and chemical biology. *Chem. Biol.* 2012, 19, 85.
30. Perlman, Z. E.; Slack, M. D.; Feng, Y.; Mitchison, T. J.; Wu, L. F.; Altschuler, S. J. Altschuler, S. J., Multidimensional drug profiling by automated microscopy. *Science.* 2004, 306, 1194.
31. Wong, W. R.; Oliver, A. G.; Linington, R. G. Development of antibiotic activity profile screening for the classification and discovery of natural product antibiotics. *Chem. Biol.* 2012, 19, 1483.
32. Wang, M.; Carver, J. J.; Phelan, V. V.; Sanchez, L. M.; Garg, N.; Peng, Y.; Nguyen, D. D.; Watrous, J.; Kapono, C. A.; Luzzatto-Knaan, T. Sharing and community curation of mass spectrometry data with Global Natural Products Social Molecular Networking. *Nat. Biotechnol.* 2016, 34, 828.
33. Watrous, J.; Roach, P.; Alexandrov, T.; Heath, B. S.; Yang, J. Y.; Kersten, R. D.; van der Voort, M.; Pogliano, K.; Gross, H.; Raaijmakers, J. M. Mass spectral molecular networking of living microbial colonies. *Proc. Natl. Acad. Sci. U.S.A.* 2012, 109, 1743.
34. Abe, H.; Yamasaki, T.; Fujiwara, I.; Sasaki, S. Computer-aided structure elucidation methods. *Anal. Chim. Acta.* 1981, 133, 499.
35. Jaspars, M. Computer assisted structure elucidation of natural products using two-dimensional NMR spectroscopy. *Nat. Prod. Rep.* 1999, 16, 241.
36. Liu, Y.; Saurí, J.; Mevers, E.; Peczuh, M. W.; Hiemstra, H.; Clardy, J.; Martin, G. E.; Williamson, R. T. Unequivocal determination of complex molecular structures using anisotropic NMR measurements. *Science.* 2017, 356.
37. Smith, S. G.; Goodman, J. M. Assigning stereochemistry to single diastereoisomers by GIAO NMR calculation: The DP4 probability. *J. Am. Chem. Soc.* 2010, 132, 12946.
38. Willoughby, P. H.; Jansma, M. J.; Hoye, T. R. A guide to small-molecule structure assignment through computation of (1H and 13 C) NMR chemical shifts. *Nat. Protoc.* 2014, 9, 643.
39. Peng, J.; Place, A. R.; Yoshida, W.; Anklin, C.; Hamann, M. T. Structure and absolute configuration of karlotoxin-2, an ichthyotoxin from the marine dinoflagellate *Karlodinium veneficum*. *J. Am. Chem. Soc.* 2010, 132, 3277.

40. Waters, A. L.; Oh, J.; Place, A. R.; Hamann, M. T. Stereochemical studies of the Karlotoxin class using NMR spectroscopy and DP4 chemical-shift analysis: insights into their mechanism of action. *Angew. Chem.* 2015, 127, 15931.

41. Nugroho, A. E.; Morita, H. Circular dichroism calculation for natural products. *J. Nat. Med.* 2014, 68, 1.

42. Li, X.-C.; Ferreira, D.; Ding, Y. Determination of absolute configuration of natural products: theoretical calculation of electronic circular dichroism as a tool. *Curr. Org. Chem.* 2010, 14, 1678.

43. Breton, R. C.; Reynolds, W. F. Using NMR to identify and characterize natural products. *Nat. Prod. Rep.* 2013, 30, 501.

44. Wang, X.; Liu, J.; Pandey, P.; Fronczek, F. R.; Doerksen, R. J.; Chen, J.; Qi, X.; Zhang, P.; Ferreira, D.; Valeriote, F. A. Computationally assisted assignment of the Kadsuraols, a class of chemopreventive agents for the control of liver cancer. *Org. Lett.* 2018, 20, 5559.

45. Wang, X.; Liu, J.; Pandey, P.; Chen, J.; Fronczek, F. R.; Parnham, S.; Qi, X.; Doerksen, R. J.; Ferreira, D.; Sun, H.; M. T. Hamann. Assignment of the absolute configuration of hepatoprotective highly oxygenated triterpenoids using X-ray, ECD, NMR J-based configurational analysis and HSQC overlay experiments *Biochim. Biophys. Acta*, Gen. Subj. 2017, 1861, 3089.

46. Kobayashi, J. I.; Cheng, J.-F.; Ishibashi, M.; Nakamura, H.; Ohizumi, Y.; Hirata, Y.; Sasaki, T.; Lu, H.; Clardy, J. Prianosin A, a novel antileukemic alkaloid from the okinawan marine sponge *Prianos melanos*. *Tetrahedron lett.* 1987, 28, 4939.

47. Perry, N. B.; Blunt, J. W.; Munro, M. H. Cytotoxic pigments from New Zealand sponges of the genus *Latrunculia*: discorhabdins A, B and C. *Tetrahedron* 1988, 44, 1727.

48. Wang, X.; Duggan, B. M.; Molinski, T. F. Mollenynes B-E from the Marine Sponge *Spirastrella mollis*. Band-Selective Heteronuclear Single Quantum Coherence for Discrimination of Bromo-Chloro Regioisomerism in Natural Products. *J. Am. Chem. Soc.* 2015, 137, 12343.

49. Cheeseman, J. R.; Trucks, G. W.; Keith, T. A.; Frisch, M. J. A comparison of models for calculating nuclear magnetic resonance shielding tensors. *J. Chem. Phys.* 1996, 104, 5497.

50. McWeeny, R. Perturbation theory for the Fock-Dirac density matrix. *Phys. Rev.* 1962, 126, 1028.

51. Wolinski, K.; Hinton, J. F.; Pulay, P. Efficient implementation of the gauge-independent atomic orbital method for NMR chemical shift calculations. *J. Am. Chem. Soc.* 1990, 112, 8251.

52. Grimblat, N. S.; Zanardi, M. M.; Sarotti, A. M. Beyond DP4: An improved probability for the stereochemical assignment of isomeric compounds using quantum chemical calculations of NMR shifts. *J. Org. Chem.* 2015, 80, 12526.

53. Radisky, D. C.; Radisky, E. S.; Barrows, L. R.; Copp, B. R.; Kramer, R. A.; Ireland, C. M. Novel cytotoxic topoisomerase II inhibiting pyrroloiminoquinones from Fijian sponges of the genus Zyzzya. *J. Am. Chem. Soc.* 1993, 115, 1632.

54. Gaussian 09, Revision A.02, M. J. Frisch, G. W. Trucks, H. B. Schlegel, G. E. Scuseria, M. A. Robb, J. R. Cheeseman, G. Scalmani, V. Barone, G. A. Petersson, H. Nakatsuji, X. Li, M. Caricato, A. Marenich, J. Bloino, B. G. Janesko, R. Gomperts, B. Mennucci, H. P. Hratchian, J. V. Ortiz, A. F. Izmaylov, J. L. Sonnenberg, D. Williams-Young, F. Ding, F. Lipparini, F. Egidi, J. Goings, B. Peng, A. Petrone, T. Henderson, D. Ranasinghe, V. G. Zakrzewski, J. Gao, N. Rega, G. Zheng, W. Liang, M. Hada, M. Ehara, K. Toyota, R. Fukuda, J. Hasegawa, M. Ishida, T. Nakajima, Y. Honda, O. Kitao, H. Nakai, T. Vreven, K. Throssell, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, J. M. Millam, M. Klene, C. Adamo, R. Cammi, J. W. Ochterski, R. L. Martin, K. Morokuma, O. Farkas, J. B. Foresman, and D. J. Fox, Gaussian, Inc., Wallingford Conn., 2016.

55. Schrödinger Release 2016-1: Maestro, Schrödinger, LLC: New York, N.Y., 2016.

56. Schrödinger Release 2016-1: LigPrep, Schrödinger, LLC: New York, N.Y., 2016.

57. X. Wang; J, Liu; P, Pandey; F. R. Fronczek; R. J Doerksen; J. Chen; X. Qi; P. Zhang; D. Ferreira; F. A. Valeriote; H. Sun; S. Li; M. T. Hamann. Computationally assisted assignment of the Kadsuraols, a class of chemopreventive agents for the control of liver cancer. *Org. Lett.* 20, 5559-5563 (2018).

58. X. Wang; J. Liu; P. Pandey; J. Chen; F. R. Fronczek; S. Parnham; X. Qi; R. J. Doerksen; D. Ferreira; H. Sun; S. Li; M. T. Hamann. Assignment of the absolute configuration of hepatoprotective highly oxygenated triterpenoids using X-ray, ECD, NMR J-based configurational analysis and HSQC overlay experiments. *Biochim. Biophy. Acta,* 1861, 3089 (2017).

59. Schrödinger Release 2016-1: MacroModel, Schrödinger, LLC: New York, N.Y., 2016.

60. Grimblat, N.; Zanardi, M. M.; Sarotti, A. M. Beyond DP4: An improved probability for the stereochemical assignment of isomeric compounds using quantum chemical calculations of NMR shifts. *J. Org. Chem.* 80, 12526-12534 (2015).

61. Desmaele, D. and Angelo, J. Stereocontrolled elaboration of quaternary carbon centers through the asymmetric Michael reaction using chiral imines: enantioselective synthesis of (+)-Aspidospermidine. *J. Org. Chem.,* 59(9), 2292-2303 (1994); Inouye, Y., Shirai, M., Michino, T. and Kakisawa, H. Preparation of an 8-membered ring via intramolecular [2+2] photocycloadduct: formal total synthesis of (±)-precapnelladiene. *Bull. Chem. Soc. Jpn.,* 66(1), 324-326 (1993)

62. Yager, K. M. (1993). "Synthetic studies on marine natural products: Part 1. Synthesis of the sesquiterpenoid dihydropallescensin D via manganese (III)-mediated carbocyclization. Part 2. Approaches toward the synthesis of prianosin and discorhabdin alkaloids." Ph.D. Dissertation, Oregon State University.

The invention claimed is:

1. A synthetic pharmaceutical formulation comprising a compound as depicted in formula (L:)

$R_1$ = S, O, $CH_2$, Se
$R_2$ = F, Cl, Br, I, H or a pharmaceutically acceptable salt thereof wherein R.sub.1=S, O, CH2, and Se and R.sub.2=F, Cl, Br, I and H and a pharmaceutically acceptable carrier or a pharmaceutically acceptable excipient.

2. The synthetic pharmaceutical formulation of claim 1, wherein the pyrroloiminoquinone alkaloid has a structural formula (II),

3. A method of inhibiting cancer cells, the method comprising contacting cancer cells with an inhibitory amount of the synthetic pharmaceutical formulation comprising a compound as depicted in formula (I:)

$R_1$ = S, O, $CH_2$, Se
$R_2$ = F, Cl, Br, I, H or a pharmaceutically acceptable salt thereof wherein R.sub.1=S, O, CH2, and Se and R.sub.2=F, Cl, Br, I and H and a pharmaceutically acceptable carrier or a pharmaceutically acceptable excipient, wherein the cancer is selected from the group consisting of: colon, pancreatic, breast, and glioblastoma.

4. The method of claim 3, wherein the synthetic pharmaceutical formulation is comprised a compound as depicted in formula (II:)

5. A method of inhibiting pancreatic cancer cells, the method comprising contacting pancreatic cancer cells with an inhibitory amount of a synthetic pharmaceutical compound of the formula:

$R_1$ = S, O, $CH_2$, Se
$R_2$ = F, Cl, Br, I, H or a pharmaceutically acceptable salt thereof.

6. The method of claim 5, wherein the pyrroloiminoquinone alkaloid has a structural formula (II), 7. The method of claim 5, wherein the pancreatic cancer is PANC-1 with an IC50 of 25 nM.

8. A method of inhibiting colon cancer cells, the method comprising contacting pancreatic cancer cells with an inhibitory amount of a synthetic pharmaceutical compound of the formula:

R₁ = S, O, CH₂, Se
R₂ = F, Cl, Br, I, H or a pharmaceutically acceptable salt thereof.

9. The method of claim 8, wherein the pyrroloiminoquinone alkaloid has a structural formula (II),

10. The method of claim 8, wherein the colon cancer is H116 with IC50 of 1 µM.

11. A method of inhibiting breast cancer cells, the method comprising contacting breast cancer cells with an inhibitory amount of the synthetic pharmaceutical formulation of R₁ = S, O, CH₂, Se
R₂ = F, Cl, Br, I, H.

12. The method of claim 11, wherein the pyrroloiminoquinone alkaloid has a structural formula (II), formula (II).

* * * * *